US00PP27308P2

(12) United States Plant Patent
Ui et al.

(10) Patent No.: US PP27,308 P2
(45) Date of Patent: Oct. 25, 2016

(54) ***PETUNIA* PLANT NAMED 'SAKPET097'**

(50) Latin Name: ***Petunia hybrida* f. cv.**
Varietal Denomination: SAKPET097

(71) Applicant: Sakata Seed Corporation, Tsuzuki-Ku, Yokohama (JP)

(72) Inventors: Akinobu Ui, Iwata (JP); Randy Holbert, Salinas, CA (US)

(73) Assignee: Sakata Seed Corporation, Yokohama (JP)

( * ) Notice: Subject to any disclaimer, the term of this patent is extended or adjusted under 35 U.S.C. 154(b) by 33 days.

(21) Appl. No.: 14/545,178

(22) Filed: Apr. 3, 2015

(51) Int. Cl.
*A01H 5/02* (2006.01)

(52) U.S. Cl.
USPC ..... Plt./356.1

(58) Field of Classification Search
USPC ..... Plt./356.1
See application file for complete search history.

*Primary Examiner* — Annette Para
(74) *Attorney, Agent, or Firm* — Bethany R. Roahrig; Barbara Campbell; Cochran Freund & Young, LLC

(57) ABSTRACT

A *petunia* plant particularly distinguished by having flowers that open dark violet and mature to a light lavender plum and a mounding habit, is disclosed.

2 Drawing Sheets

Genus and species: *Petunia hybrida* f. cv.
Variety denomination: 'SAKPET097'.

BACKGROUND OF THE NEW PLANT

The present invention comprises of a new and distinct variety of *petunia*, botanically known as *Petunia hybrida* f. cv., and hereinafter referred to by the variety name 'SAKPET097.' 'SAKPET097' is characterized by flowers which open dark violet and mature to light lavender plum with a mounding plant habit. *Petunia* variety 'SAKPET097' originated from a hybridization in Kakegawa, Japan in 2009. The female parent was an unnamed proprietary *petunia* breeding line (unpatented) having a blue and white star-patterned bicolored flowers and a semi-mounding plant habit. The male parent was an unnamed proprietary *petunia* breeding line (unpatented) having rose pink flowers and a creeping plant habit.

In June 2009, two breeding lines were crossed, female line 'PCB-1' and male line '6Bcr-135a-2a' and 100 seeds were obtained. In February 2010 100 seeds were sown and 30 plants were cultivated. The plants had flower colors of blue and white star-pattern, rose and white star pattern, light magenta and magenta with plant habits of creeping, semi-creeping and semi-mounding. In June 2010, 2 plants were crossed and approximately 1,500 seeds were obtained. One plant had a blue and white star-pattern with a semi-creeping plant habit. The other plant had a magenta and white star-pattern with a mounding plant habit. In November 2010, 1,000 seeds from the $F_2$ plants were sown and cultivated for evaluation. In March 2011, a plant line was selected within the $F_2$ plants that had flowers that open dark violet and mature to a light lavender plum and a mounding plant growth habit. The selection was named 'L2011-249'. From February through March 2011 the selection was evaluated for day length neutral flowering response in Salinas, Calif. In March 2011, 'L2011-249' was first vegetatively propagated and cultivated in Salinas, Calif., and in May 2011 transplanted to the field for outdoor evaluation. From June 2011 to October 2011, and in January 2012, the breeder confirmed that line 'L2011-205' was fixed and stable. The line was subsequently named 'SAKPET097' and its unique characteristics were found to reproduce true to type in successive generations of asexual propagation via vegetative cuttings.

SUMMARY

The following are the most outstanding and distinguishing characteristics of this new variety when grown under normal horticultural practices in Salinas, Calif.

1. Flowers which open dark violet and mature to light lavender plum; and
2. A mounding growth habit.

DESCRIPTION OF THE PHOTOGRAPHS

This *petunia* plant is illustrated by the accompanying photographs which show the plant's overall plant habit including form, foliage, and flowers. The photographs are of a 5 month old plant grown in Salinas, Calif. under greenhouse conditions in the spring of 2014. The colors shown are as true as can be reasonably obtained by conventional photographic procedures.

DESCRIPTION OF THE NEW VARIETY

Figure 1:
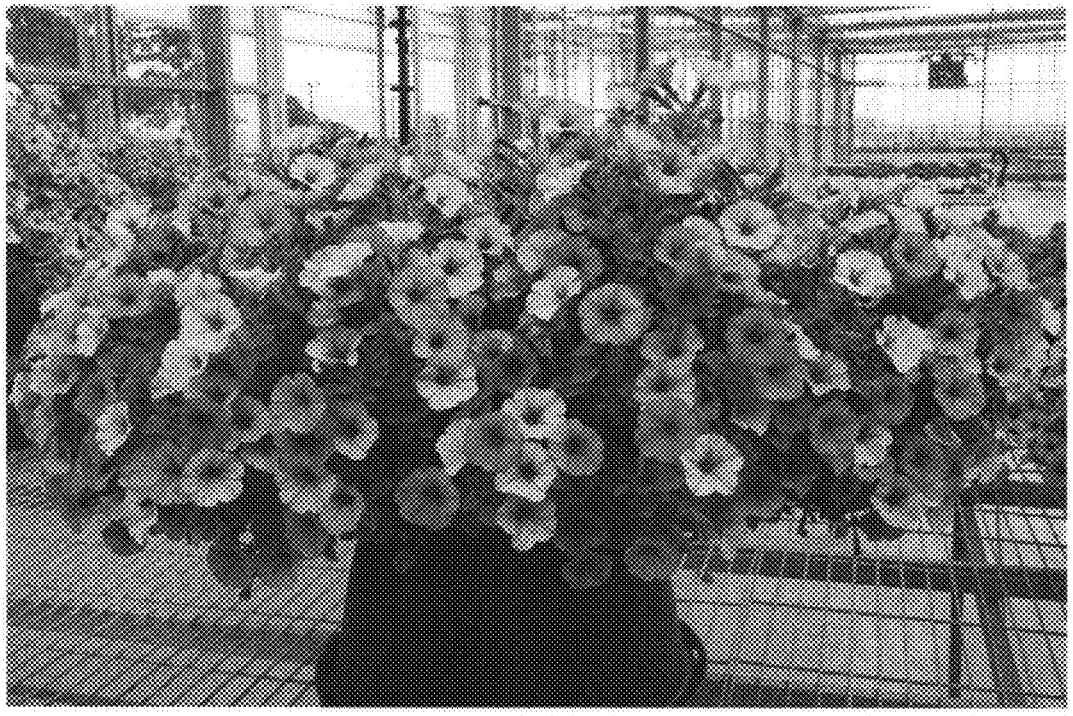
FIG. 1 shows the overall plant habit of the plant grown in a pot.
Figure 2:
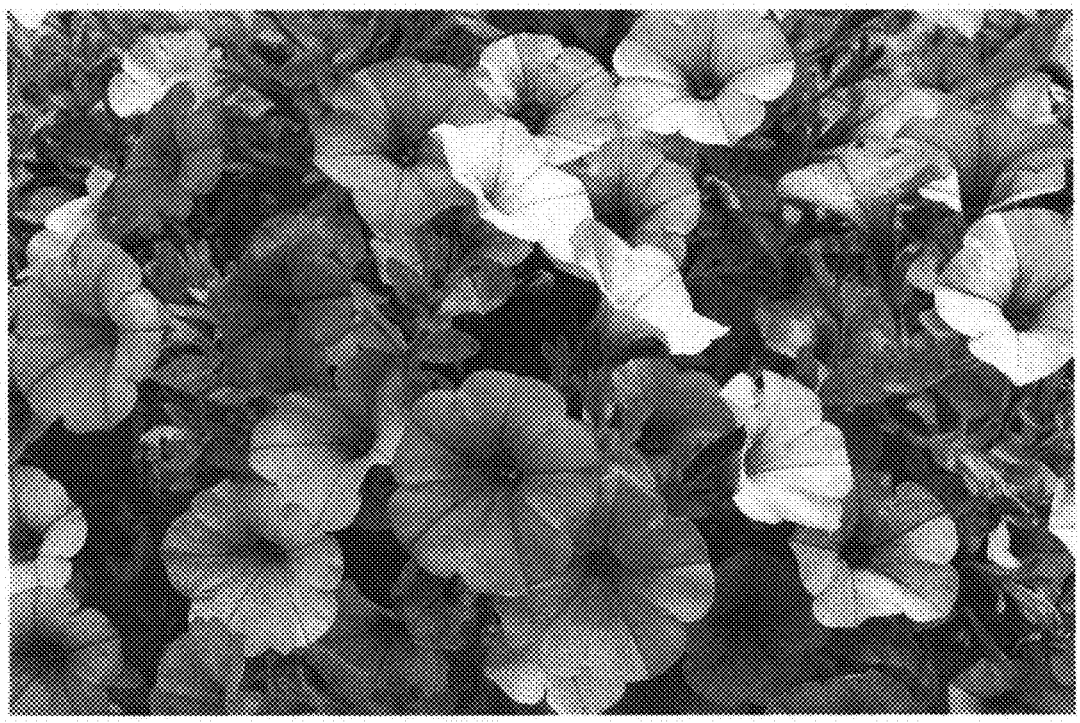
FIG. 2 shows a close-up of the mature inflorescences of the plant.

The following detailed descriptions set forth the distinctive characteristics of 'SAKPET097'. Data was collected on plants grown 5 months from transplant into 8-inch posts from rooted cuttings in Salinas, Calif., under greenhouse conditions in the spring 2014. Plants were pinched once during growth. Color references are to The Royal Horticultural Society of London Colour Chart (R.H.S.), $4^{th}$ edition (2001). Anatomic labels are from *The Cambridge Illustrated Glossary of Botanical Terms*, by M. Hickey and C. King, Cambridge University Press.

Classification:

*Family*.—Solanaceae.

*Botanical*.—*Petunia hybrida* f. cv.

*Common*.—*Petunia*.

*Designation*.—'SAKPET097'.

Parentage:

*Female parent*.—Unnamed proprietary *petunia* breeding line (unpatented) having a blue and white star-patterned bicolored flowers.

*Male parent*.—Unnamed proprietary *petunia* breeding line (unpatented) having magenta and white star-patterned flowers.

Growth:

*Time to produce a rooted cutting*.—About 4 weeks.

*Environmental conditions for plant growth*.—The terminal 1.0 to 1.5 inches of an actively growing stem was excised. The vegetative cuttings were propagated for five to six weeks. The base of the cuttings were dipped for 1 to 2 seconds in a 1:9 solution of DIP 'N GROW (1 solution:9 water) root inducing solution immediately prior to sticking into the cell trays. Cuttings were stuck into plastic cell trays having 98 cells, and containing a moistened peat moss-based growing medium. The cuttings were misted with water from overhead for 10 seconds every 30 minutes until sufficient roots were formed. Rooted cuttings were transplanted and grown in 20 cm diameter plastic pots in a glass greenhouse located in Salinas, Calif. Pots contained a peat moss-based growing medium. Soluble fertilizer containing 20% nitrogen, 10% phosphorus and 20% potassium was applied once a day or every other day by overhead irrigation. Pots were top-dressed with a dry, slow release fertilizer containing 20% nitrogen, 10% phosphorus and 18% potassium. The typical average air temperature was 24° C.

Plant description:

*Form*.—Decumbent (trailing).

*Habit*.—Mounding.

*Height*.—About 24.0 cm from soil line to top of foliage.

*Spread*.—About 85.0 cm.

*Number of branches*.—About 8 main basal branches; many secondary and tertiary branches.

*Length of branches*.—30.0 cm.

*Diameter of branches*.—3.0 mm.

*Life cycle*.—Annual; tender perennial in warm climates.

*Time to bloom from propagation*.—6 to 8 weeks.

*Flowering requirements* (*season*).—Will flower so long as temperature is above 13° C. and greater than 12 hours of daylight.

*Temperature tolerances*.—No particular temperature tolerances observed.

Stems:

*Stem color*.—RHS 143A (Green).

*Anthocyanin color*.—Moderate, RHS N187A (Greyed-Purple).

*Stem pubescence*.—Heavy.

*Stem pubescence color*.—RHS N155A (White).

*Stem description*.—Pliable; circular cross-section.

*Stem length*.—About 21.0 cm.

*Stem diameter*.—About 2.0 mm.

*Internode length*.—About 2.0 cm.

Leaves:

*Leaf arrangement*.—Alternate.

*Leaf shape*.—Ovate.

*Leaf apex*.—Obtuse.

*Leaf base*.—Attenuate.

*Leaf attachment*.—Sessile.

*Leaf margin*.—Entire.

*Leaf surface*.—Dull, waxy and sticky with slight pubescence.

*Leaf length*.—3.0 cm.

*Leaf width*.—2.2 cm.

*Leaf color*.—Upper: RHS 146A (Yellow-Green). Lower: RHS 146B (Yellow-Green).

*Leaf variegation*.—Absent.

*Leaf fragrance*.—Absent.

*Leaf surface pubescence*.—Slight.

*Leaf surface pubescence color*.—RHS N155A (White).

*Petiole*.—Absent.

*Venation*.—Pinnate.

*Venation color* (*both surfaces*).—RHS 144A (Yellow-Green).

Inflorescence:

*Number of flowers per node*.—1.

*Inflorescence type*.—Solitary.

*Fragrance*.—Absent.

*Flower depth*.—0.5 cm.

*Flower diameter*.—3.5 cm.

Corolla:

*Corolla shape*.—Funnel-shaped with 5 fused petals.

*Corolla diameter*.—8.0 mm.

*Corolla depth*.—0.5 cm.

*Corolla tube length*.—2.5 cm.

*Corolla tube diameter*.—8.0 mm.

*Corolla tube pubescence*.—Heavy.

*Corolla tube pubescence color*.—RHS N155A (White).

*Corolla tube color*.—Inner surface: 3 main colors from darkest to lightest: 1. RHS 79C (Purple) with RHS N77A (Purple) veins. 2. RHS 79B (Purple) with RHS N77A (Purple) veins. 3. RHS 83B (Violet) with RHS 83A (Violet) at the mid-vein. Outer surface: 3 main colors from darkest to lightest: 1. RHS 79B (Purple) with RHS N77A (Purple) veins. 2. RHS 83B (Violet) with RHS N77A (Purple) veins. 3. RHS 83A (Violet).

Calyx:

*Sepal number*.—5, free.

*Sepal attachment*.—Sessile.

*Sepal apex*.—Obtuse.

*Sepal base*.—Attenuate.

*Sepal margin*.—Entire.

*Sepal length*.—1.4 cm.

*Sepal width*.—3.0 mm.

*Sepal color* (*both surfaces*).—RHS 144A (Yellow-Green).

Bud:

*Bud surface*.—Dull, sticky, heavy pubescence; pubescence color is RHS N155A (White).

*Bud length*.—2.8 cm.

*Bud diameter*.—4.0 mm.

*Bud shape*.—Cylindrical.

*Bud color*.—RHS 83A (Violet).

Peduncle:

*Peduncle length.*—3.0 cm.

*Peduncle diameter.*—1.0 mm.

*Peduncle color.*—RHS 144A (Yellow-Green) with slight anthocyanin, RHS N77A (Purple).

Petals:

*Petal pubescence.*—Glabrous.

*Petal length.*—2.0 cm.

*Petal width.*—2.0 cm.

*Petal shape.*—Obcordate.

*Petal apex.*—Acuminate.

*Petal margin.*—Entire.

*Petal color.*—Upper surface: 3 main colors from darkest to lightest: 1. RHS N78A (Purple) with RHS N77A (Purple) at the mid-vein. 2. RHS N78B (Purple) with N77A (Purple) at the mid-vein. 3. RHS N155A (White) and RHS 83A (Violet) at tip and at the mid-vein. Lower surface: 3 main colors from darkest to lightest: 1. RHS N82C (Purple-Violet) with RHS N77A (Purple) at the mid-vein. 2. RHS 82C (Purple-Violet) with RHS N77A (Purple) at the mid-vein. 3. RHS N82C (Purple-Violet) with RHS 83A (Violet) at the mid-vein.

Reproductive organs:

*Stamens.*—Stamen form: Arranged adjacent to pistil. Stamen number: 5, free. Stamen length: 1.0 cm. Filament color: RHS 84B (Violet). Anther color: Closest to RHS 94A (Violet-Blue).

*Pistil.*—Pistil number: 1. Pistil length: 1.5 cm. Stigma color: RHS 83C (Violet) with RHS 139A (Green) at tip. Stigma length: 2.0 mm. Style color: RHS 145B (Yellow-Green). Style length: 1.5 cm.

*Ovary.*—Ovary arrangement: Superior. Ovary surface color: RHS 144A (Yellow-Green).

*Pollen.*—Pollen amount: Abundant. Pollen description: Powdery. Pollen color: RHS 97A (Violet-Blue).

Seed production: Absent.

Disease and insect resistance: No particular resistance or susceptibility observed.

COMPARISON WITH PARENTAL LINES AND KNOWN VARIETY

'SAKPET097' is a new and distinct variety of *petunia* having flowers that open dark violet and mature to a light lavender plum and a mounding plant growth habit. Due to its bouquet of colors on a single plant, 'SAKPET097' does not have a known close commercial comparison, but could be considered somewhat similar to the commercial variety, 'Balspunlar', also known as SUN SPUN 'Lavender Star' *Petunia* (unpatented); however, there are differences as listed in Table 1 below:

TABLE 1

Comparison with Similar Variety

| Characteristic | 'SAKPET097' | SUN SPUN 'Lavender Star' |
|---|---|---|
| Petal color, upper surface | 3 main colors from darkest to lightest:<br>1. RHS N78A (Purple) with RHS N77A (Purple) at mid-vein<br>2. RHS N78B (Purple) with N77A (Purple) at mid-vein<br>3. RHS N155A (White) and RHS 83A (Violet) at tip and at mid-vein | Closest to, but darker than the lightest color of 'SAKPET097' which is RHS N155A (White) and RHS 83A (Violet) at tip and at mid-vein |
| Petal color, lower surface | 3 main colors from darkest to lightest:<br>1. RHS N82C (Purple-Violet) with RHS N77A (Purple) at mid-vein<br>2. RHS 82C (Purple-Violet) with RHS N77A (Purple) at mid-vein<br>3. RHS N82C (Purple-Violet) with RHS 83A (Violet) at mid-vein | RHS 79C (Violet) with N155D (White) |
| Flower diameter | 3.5 cm | Larger than 'SAKPET097' |
| Plant growth habit | Mounding | Tight, compact, ball-shaped habit |

'SAKPET097' differs from the parental lines as described in Table 2 below.

TABLE 2

Comparison with Parental Lines

| Characteristic | 'SAKPET097' | Unnamed female | Unnamed male |
|---|---|---|---|
| Flower color | Open dark violet and mature to a light lavender plum | Blue and white star-patterned bicolored flowers | Magenta and white star-patterned flowers |
| Plant growth habit | Mounding | Semi-creeping | Mounding |

We claim:

1. A new and distinct variety of *petunia* plant named 'SAKPET097' as described and illustrated herein.

* * * * *